United States Patent
Taghizadeh

(10) Patent No.: US 9,920,301 B2
(45) Date of Patent: *Mar. 20, 2018

(54) NATIVE WHARTON'S JELLY STEM CELLS AND THEIR PURIFICATION

(71) Applicant: Auxocell Laboratories, Inc., Cambridge, MA (US)

(72) Inventor: Rouzbeh R. Taghizadeh, Cambridge, MA (US)

(73) Assignee: Auxocell Laboratories, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/393,999

(22) Filed: Dec. 29, 2016

(65) Prior Publication Data

US 2017/0107496 A1    Apr. 20, 2017

Related U.S. Application Data

(60) Continuation of application No. 15/241,585, filed on Aug. 19, 2016, which is a division of application No. 14/667,039, filed on Mar. 24, 2015, now Pat. No. 9,441,201, which is a continuation of application No. 13/752,928, filed on Jan. 29, 2013, now Pat. No. 9,012,222, which is a continuation of application No. 13/701,329, filed as application No. PCT/US2011/038710 on Jun. 1, 2011, now abandoned.

(60) Provisional application No. 61/350,303, filed on Jun. 1, 2010.

(51) Int. Cl.

| | | |
|---|---|---|
| C12N 5/02 | (2006.01) |
| C12N 5/07 | (2010.01) |
| C12N 5/00 | (2006.01) |
| C12N 5/0775 | (2010.01) |
| C12N 5/073 | (2010.01) |
| C12N 5/071 | (2010.01) |

(52) U.S. Cl.
CPC ............. *C12N 5/0668* (2013.01); *C12N 5/00* (2013.01); *C12N 5/06* (2013.01); *C12N 5/0602* (2013.01); *C12N 5/0605* (2013.01); *C12N 5/0662* (2013.01); *C12N 2500/84* (2013.01); *C12N 2502/025* (2013.01)

(58) Field of Classification Search
None
See application file for complete search history.

(56) References Cited

U.S. PATENT DOCUMENTS

| | | |
|---|---|---|
| 5,731,199 A | 3/1998 | Roggero et al. |
| 5,811,094 A | 9/1998 | Caplan et al. |
| 5,919,702 A | 7/1999 | Purchio et al. |
| 6,355,239 B1 | 3/2002 | Bruder et al. |
| 6,387,367 B1 | 5/2002 | Davis-Sproul et al. |
| 6,835,377 B2 | 12/2004 | Goldberg et al. |
| 7,491,384 B2 | 2/2009 | Hart et al. |
| 7,736,892 B2 | 6/2010 | Weiss et al. |
| 7,807,458 B2 | 10/2010 | Schiller et al. |
| 8,034,329 B2 | 10/2011 | Colter et al. |
| 8,105,634 B2 | 1/2012 | Liu et al. |
| 8,703,411 B2 | 4/2014 | Chang et al. |
| 9,012,222 B2 | 4/2015 | Taghizadeh |
| 2003/0161818 A1 | 8/2003 | Weiss et al. |
| 2004/0193071 A1 | 9/2004 | Binette et al. |
| 2005/0139704 A1 | 6/2005 | Liao et al. |
| 2008/0019949 A1 | 1/2008 | Mitchell et al. |
| 2008/0118477 A1 | 5/2008 | Christopherson |
| 2008/0226595 A1 | 9/2008 | Edinger et al. |
| 2009/0269318 A1 | 10/2009 | Davies et al. |
| 2010/0111908 A1 | 5/2010 | Lin et al. |
| 2010/0216237 A1 | 8/2010 | Ganchas Soares et al. |
| 2011/0151556 A1 | 6/2011 | Kallis et al. |
| 2011/0293576 A1 | 12/2011 | Lange et al. |
| 2012/0276070 A1 | 11/2012 | Musick |
| 2013/0121972 A1 | 5/2013 | Taghizadeh |
| 2013/0183273 A1 | 7/2013 | Taghizadeh |
| 2013/0202566 A1 | 8/2013 | Park et al. |
| 2013/0259840 A1 | 10/2013 | Davies et al. |
| 2013/0295673 A1 | 11/2013 | Taghizadeh et al. |

FOREIGN PATENT DOCUMENTS

| | | |
|---|---|---|
| CN | 101575590 A | 11/2009 |
| CN | 101629165 A | 1/2010 |
| CN | 101642469 A | 2/2010 |
| CN | 101643719 A | 2/2010 |
| WO | WO-2008002662 A2 | 1/2008 |
| WO | WO-2008060377 A2 | 5/2008 |
| WO | WO-2010040865 A1 | 4/2010 |
| WO | WO-2011153205 A1 | 12/2011 |
| WO | WO-2012131618 A1 | 10/2012 |
| WO | WO-2013070899 A1 | 5/2013 |

OTHER PUBLICATIONS

"Autologous vs Allogenic Stem Cell Transplant" (2007) [Retrieved on Feb. 20, 2014] Retrieved from the Internet: <URL: https://web.archive.org/web/20071020015656/http://www.wdxcyber.com/versus.html>.

Anzalone et al., (2010) "New emerging potentials for human Wharton's jelly mesenchymal stem cells: immunological features and hepatocyte-like differentiative capacity," *Stem Cells and Development*. 19:423-438.

Cetrulo et al., (2010) "Wharton's jelly stem cells: a novel source for tomorrow's cellular therapies," International Society for Cellular Therapy. 17(1):31 pages.

Chao et al., (2008) "Islet-Like Clusters Derived from Mesenchymal Stem Cells in Wharton's Jelly of the Human Umbilical Cord for Transplantation to Control Type 1 Diabetes," *PLoS One*. 3(1): e1451, 9 pages.

(Continued)

*Primary Examiner* — Jennifer Pitrak McDonald
*Assistant Examiner* — Qing Xu
(74) *Attorney, Agent, or Firm* — Goodwin Procter LLP

(57) ABSTRACT

Noncultured Wharton's Jelly stem cells and methods of their purification, storage and use are provided.

1 Claim, 3 Drawing Sheets

(56) References Cited

OTHER PUBLICATIONS

De Bruyn et al., (2011) "A Rapid, Simple, and Reproducible Method for the Isolation of Mesenchymal Stromal Cells from Wharton's Jelly Without Enzymatic Treatment," *Stem Cells and Development*. 20(3):547-557.
Final Office Action for U.S. Appl. No. 13/752,928, dated Mar. 21, 2014, 21 pages.
Fong et al., (2007) "Comparative growth behaviour and characterization of stem cells from human Wharton's jelly," *Reproductive BioMedicine Online*. 15(6):708-718.
Fong et al., (2010) "Derivation efficiency, cell proliferation, freeze-thaw survival, stem-cell properties and differentiation of human Wharton's jelly stem cells," *Reproductive BioMedicine Online*. 21:391-401.
Friedman et al., (2007) "Umbilical Cord Mesenchymal Stem Cells: Adjuvants for Human Cell Transplantation," *Biology of Blood and Marrow Transplantation*. 13:1477-1486.
International Search Report and Written Opinion for PCT/US2011/038710, dated Oct. 31, 2011, 18 pages.
International Search Report and Written Opinion for PCT/US2012/064130, dated Jan. 25, 2013, 16 pages.
Kilian et al., (2004) "Effects of platelet growth factors on human mesenchymal stem cells and human endothelial cells in vitro," *Eur J Med Res*. 9:337-344.
Koliakos et al., (2011) "Mesenchymal cells isolation from Wharton's jelly, in perspective to clinical applications," *Journal of Biological Research-Thessaloniki*. 16:194-201.
La Rocca et al., (2009) "Isolation and characterization of Oct-4+/HLA-G+ mesenchymal stem cells from human umbilical cord matrix: differentiation potential and detection of new markers," *Histochem Cell Biol*. 131:267-282.
Lu et al., (2006) "Isolation and Characterization of Human Umbilical Cord Mesenchymal Stem Cells with Hematopoiesis-Supportive Function and Other Potentials," *The Hematology Journal*. 91(8):1017-1026.
Montanucci et al., (2011) "New Simple and Rapid Method for Purification of Mesenchymal Stem Cells from the Human Umbilical Cord Wharton Jelly," *Tissue Engineering Part A*. 17(21-22):2651-2661.
Moretti et al., (2010) "Mesenchymal stromal cells derived from human umbilical cord tissues: primitive cells with potential for clinical and tissue engineering applications," *Advances in Biochemical*. 123:29-54.
Ng et al., (2008) "PDGF, TGF-13, and FGF signaling is important for differentiation and growth of mesenchymal stem cells (MSCs): transcriptional profiling can identify markers and signaling pathways important in differentiation of MSCs into adipogenic, chondrogenic, and osteogenic lineages," *Blood*. 112:295-307.
Noort et al., (2002) "Mesenchymal stem cells promote engraftment of human umbilical cord blood-derived CD34+ cells in NOD/SCID mice," *Experimental Hematology*. 30:870-878.
Office Action for U.S. Appl. No. 13/752,928, dated Jun. 26, 2013, 18 pages.
Schugar et al., (2009) "High harvest yield, high expansion, and phenotype stability of CD146 mesenchymal stromal cells from whole primitive human umbilical cord tissue," *J. of Biomedicine & Biotechnology*. 2009:Article ID 789526, 11 pages.
Seshareddy et al., (2008) "Method to isolate mesenchymal-like cells from Wharton's jelly of umbilical cord," *Methods in Cell Biology*. 86:101-119.
Singapore Search Report and Written Opinion for 201208850-6, dated Jan. 7, 2014, 14 pages.
Sobolewski et al., (2005) "Wharton's jelly as a reservoir of peptide growth factors," *Placenta*. 26:747-752.
Taghizadeh et al., (2011) "Wharton's Jelly stem cells: Future clinical applications," *Placenta*. 32 Suppl 4:S311-5.
Wang et al., (2004) "Mesenchymal stem cells in the Wharton's jelly of the human umbilical cord," *Stem Cells*. 22:1330-1337.
Weiss et al., (2006) "Human umbilical cord matrix stem cells: preliminary characterization and effect of transplantation in a rodent model of Parkinson's Disease," *Stem Cells*. 24:781-792.
Canadian Office Action for Application No. 2,801,009, dated Feb. 7, 2017 (4 pages).
Meyer, Frank, "Wharton's Jelly of the Umbilical Cord", Extracellular Matrix, vol. 1: Tissue Function, 1996 (16 pages).

NATIVE WHARTON'S JELLY STEM CELLS AND THEIR PURIFICATION

CROSS-REFERENCE TO RELATED APPLICATIONS

This application is a continuation of U.S. patent application Ser. No. 15/241,585, filed Aug. 19, 2016, which is a divisional of U.S. patent application Ser. No. 14/667,039, filed Mar. 24, 2015, which is a continuation of U.S. patent application Ser. No. 13/752,928, filed Jan. 29, 2013, which is a continuation of U.S. patent application Ser. No. 13/701,329, filed Jan. 29, 2013, which is the U.S. national stage of international patent application PCT/US2011/038710, filed Jun. 1, 2011, which claims the benefit of and priority to U.S. Provisional Application No. 61/350,303, filed Jun. 1, 2010, the disclosures of which are hereby incorporated by reference in their entireties.

BACKGROUND OF THE INVENTION

Umbilical cord tissue is a rich source of stem cells. Blood from the umbilical cord includes stem cells, including hematopoietic stem cells that can be used to repopulate a person's blood and immune system. Wharton's Jelly, a gelatinous substance within the umbilical cord, contains an additional population of stem cells, distinct from those found in cord blood. As used herein, "Wharton's Jelly" can further include the amniotic epithelial layer of the umbilical cord. Processing and culturing the Wharton's Jelly permits the isolation of mesenchymal stem cells that can be used to regenerate a variety of tissues (see, for example, U.S. Pat. No. 5,919,702).

SUMMARY OF THE INVENTION

The present inventors have discovered that the process of culturing cells from Wharton's Jelly substantially changes the characteristics of the cells. Compared to a population of cells cultured in vitro, uncultured Wharton's Jelly cells are molecularly different as can be seen, for example, in a different molecular profile on their cell surfaces. More importantly, the inventors have found that minimally manipulated Wharton's Jelly cells are substantially more potent in vivo than are cultured Wharton's Jelly cells.

The inventors have developed a method for purifying stem cells from Wharton's Jelly without the need for a culturing step. The method includes separating native, non-cultured Wharton's Jelly stem cells from a digested tissue that includes Wharton's Jelly. The method can also include a prior step of digesting the tissue, for example by mechanically mincing the tissue or exposing it to a chemical or an enzyme such as a protease, for example, a collagenase, a hyaluronidase, or a dispase, separately or in combination. In addition, the method can include mechanically increasing the surface area of the tissue, such as by cutting or mincing the tissue, tearing it into small strands or microscopic pieces, or otherwise physically manipulating the tissue, prior to chemical or enzymatic digestion of the tissue. Furthermore, prior to digesting the tissue that includes Wharton's Jelly, the tissue is optionally dissected to remove arteries and veins.

Incomplete digestion can leave fragments of undigested tissue. The method can include separating the digested and undigested tissue, such as by sedimenting the undigested tissue. The sedimentation process can be accelerated by, for example, centrifugation. Alternatively, the digested tissue can be filtered to remove the undigested tissue; the noncultured Wharton's Jelly stem cells can be separated from the filtrate, such as by sedimentation or filtration. In some embodiments, the digested tissue, which can be viscous, is washed or diluted before a separating step, although other steps such as vigorous centrifugation can be effective even in the absence of a washing or diluting step.

The inventors have also developed methods of recovering both cultured and noncultured stem cells from Wharton's Jelly. The method includes purifying noncultured Wharton's Jelly stem cells according to any of the methods described above, and culturing mesenchymal stem cells from the undigested tissue. In this manner, the uncultured stem cells of superior potency are obtained from the digested tissue and additional cells are cultured from the remnants of undigested tissue. The mesenchymal stem cells are optionally cultured in a medium that includes Wharton's Jelly.

The invention also relates to the purified, noncultured Wharton's Jelly stem cells and their use. As used herein, "purified" indicates that the Wharton's Jelly stem cells have been isolated and separated from certain acellular components of Wharton's Jelly, but does not indicate that the stem cells have necessarily been purified from other cell types that may also be present in Wharton's Jelly. In some embodiments, the purified, noncultured Wharton's Jelly stem cells are substantially free of semi-solid Wharton's Jelly. Some degree of liquefied Wharton's Jelly (digested into a viscous liquid, for example) may remain, or the cells may be entirely free of Wharton's Jelly and optionally in another medium, such as a sterile solution, a balanced salt solution, a cryoprotectant solution, plasma, etc. In other embodiments, the purified Wharton's Jelly stem cells are maintained at a temperature below 0° C., below −20° C., below −80° C., or below −180° C., for example in a vial, bag, or other container suitable at such a temperature. The purified, noncultured Wharton's Jelly stem cells of the invention can differ substantially from mesenchymal stem cells cultured from Wharton's Jelly, including differences in the level of cell surface expression of one (or two or three or four or more) of CD49B, CD105, CD133, HLA-ABC, CD73, CD44, SSEA-4, CD29, and/or CD90. In some embodiments, for example, the population of noncultured Wharton's Jelly stem cells has reduced levels of CD73 and CD105 cell surface expression compared to mesenchymal stem cells cultured from Wharton's Jelly. Both CD73 and CD105 have been reported to be markers for mesenchymal stem cells. Accordingly, the reduced level of CD73 and CD105 on the cell surfaces of noncultured Wharton's Jelly stem cells is consistent with the identification of these cells as substantially different from cultured mesenchymal stem cells.

The uncultured Wharton's Jelly stem cells are multipotent and can be administered to a subject as a part of a therapeutic method, for example, to heal a tissue or to assist in tissue regeneration. In certain embodiments, the Wharton's Jelly stem cells are advantageously autologous or allogenic to the subject.

The invention also provides a homogenous solution including Wharton's Jelly. The solution can be obtained, for example, by digesting the Wharton's Jelly to render it a viscous liquid and purifying particulates, such as undigested tissue or cells, from the digest to obtain a homogeneous solution. The solution can optionally be diluted, such as by a balanced salt solution or other sterile solution, to reduce viscosity. The solution can be depleted of cells, either by removing substantially all of the cells or by otherwise reducing the number of cells in the solution. The solution can be frozen (for example, at a temperature of −20° C. or below), and can optionally be used in a cell culture process. Thus, the invention also provides methods of maintaining a cell by mixing the cell in a homogeneous solution including Wharton's Jelly, for example by adding the cell to the solution; by adding the solution to a suspension comprising the cell; or by applying the solution to a surface to which the cell has adhered. The cell can be cultured in vitro. In one embodiment, the cell is a multipotent stem cell, such as a mesenchymal stem cell from Wharton's Jelly.

BRIEF DESCRIPTION OF THE FIGURES

Other features and advantages of the present invention, as well as the invention itself, can be more fully understood from the following description of the various embodiments, when read together with the accompanying drawings, in which.

DETAILED DESCRIPTION

Figure 1:
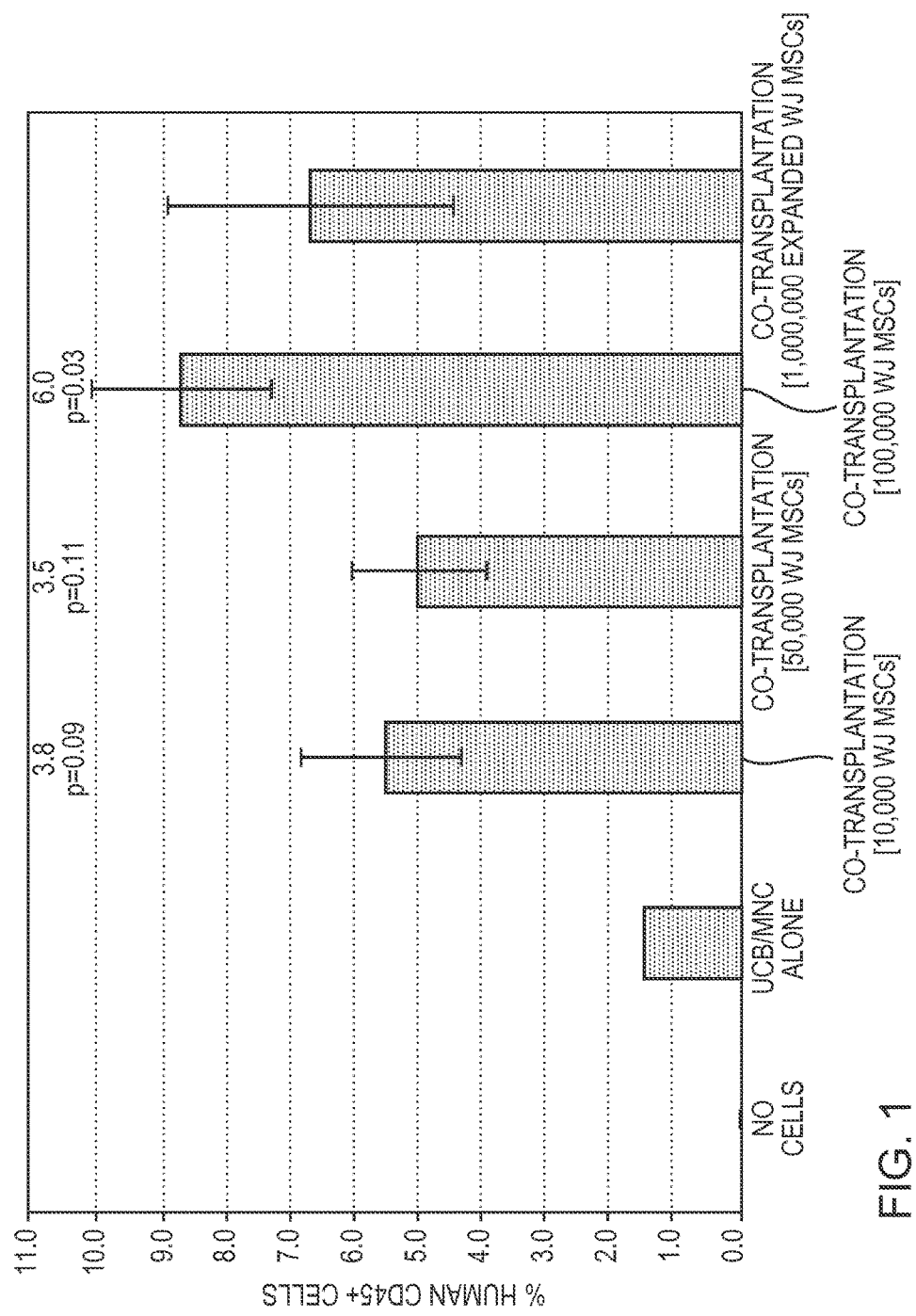
FIG. 1 graphically depicts the in vivo efficacy of noncultured Wharton's Jelly stem cells (WJ MSCs) or culture-expanded mesenchymal stem cells (Expanded WJ MSCs) in a co-transplantation assay with human hematopoietic stem cells from umbilical cord blood, with results shown as a % of bone marrow cells expressing human CD45 on their surface, which serves as a surrogate marker for engraftment of human cells transplanted into mice.

The present application provides methods for purifying Wharton's Jelly stem cells without the need for a culturing step. The resulting cells are particularly useful therapeutically, having superior potency when compared to stem cells expanded in culture from Wharton's Jelly. The application also provides a homogeneous solution from Wharton's Jelly that can be used, for example, in a process of maintaining cells, such as in culture.

To provide an overall understanding of the invention, certain illustrative embodiments will now be described. However, it will be understood by one of ordinary skill in the art that the compositions and methods described herein may be adapted and modified as appropriate and may be employed in other suitable applications. All such adaptations and modifications are to be considered within the scope of the invention.

Purification of Noncultured Wharton's Jelly Stem Cells

The purification of the Wharton's Jelly stem cells requires separating the noncultured cells from a digested tissue that includes Wharton's Jelly. The digested tissue can be processed chemically. For example, the digested tissue may result from enzymatic digestion of umbilical cord tissue, such as by a collagenase and/or another protease, such as a hyaluronidase and/or a dispase. In another example, tissue digestion may be facilitated by acids. Optionally, an umbilical cord tissue can be dissected to remove the arteries and veins, and then processed to maximize the available surface area. This processing can generally involve any manner of mechanically increasing the surface area of the tissue, but most often involves finely cutting or microscopically mincing the tissue into small strands or microscopic pieces, such as with dissecting scissors or a scalpel.

Before the cells are separated from the digested tissue, any remaining fragments of undigested tissue are optionally discarded to facilitate the subsequent purification of the cells. Depending on their size, undigested tissue could be removed by physical extraction (e.g. with forceps), decanting, aspiration, sedimentation (optionally accelerated by centrifugation), or filtering, for example.

The separation of the cells from the digested tissue can be accomplished by sedimentation of the cells from a homogeneous mixture containing the digested tissue. Although gravity sedimentation can be used, the sedimentation process can be accelerated by, for example, a centrifuge to enhance the downward movement of the cells through (and, in some sense, out of) the mixture. One such process is described in Example 1. Upon separation, the Wharton's Jelly stem cells are substantially free of the Wharton's Jelly. Because the digested tissue is generally viscous, the tissue can be washed or diluted with an appropriate sterile solution (such as a buffered salt solution) at any stage in the process. In fact, after the cells have been separated from the mixture, further washes can be performed to further cleanse the cells as desired.

Native Wharton's Jelly Stem Cells

The purified, noncultured Wharton's Jelly stem cells can be used immediately in a patient, if there is an immediate need. Typically, however, the cells are cryopreserved in liquid nitrogen until needed, typically with a cryprotectant such as DMSO or dextran, and often in a solution such as autologous plasma or 5% human serum albumin. As multipotent stem cells, the noncultured Wharton's Jelly stem cells can be used to treat or regenerate any of a variety of tissues such as bone, cartilage, fat or muscle. These cells can facilitate hematopoietic engraftment and have the potential to regulate and suppress immune responses in the host.

As described in Example 4, a population of purified noncultured cells from Wharton's Jelly is demonstrably different, at the molecular level, from a population of cells from Wharton's Jelly that have been expanded in culture ex vivo. For example, although both populations include cells expressing CD49B, CD105, HLA-ABC, CD73, CD44, SSEA-4, CD29, and CD90, the populations differ in their expression profiles for most if not all of these markers. Thus, these or other markers can be used, individually or in combination (such as any two, three, four, five, six, seven, or all eight of these markers), to identify and characterize a population of stem cells, such as those derived from umbilical cord tissue, and/or to characterize the biological potency of the cells.

Additional Products

The purification process also typically yields additional useful products. For example, when the cells are separated from the digested tissue, the remaining, cell-depleted digested tissue is a rich, sterile solution that can be used for maintaining cells (in culture, for example). It is appreciated that some cells may be present, although in substantially reduced numbers, within this rich, sterile, cell-depleted solution derived from the digested tissue. Alternatively, the solution may be completely devoid of cells. This homogeneous solution can be frozen (for example, at −20° C. or below) for later use.

Any fragments of undigested tissue remaining after a digestion process are also particularly useful, as these can be used as a source of cultured mesenchymal stem cells using standard methods for expanding mesenchymal stem cells in culture from Wharton's Jelly. In fact, the homogeneous Wharton's Jelly solution that is, in some sense, a byproduct of the purification process can be used in the culturing of mesenchymal stem cells from the undigested tissue fragments. In this way, the purification process whose primary purpose is the preparation of noncultured Wharton's Jelly stem cells can also provide, as an added benefit, mesenchymal stem cells that are expanded in culture from the undigested tissue fragments with the help of the cell-depleted Wharton's Jelly solution.

Accordingly, this invention provides two sources for the seeding and derivation of culture expanded Wharton's Jelly derived mesenchymal stem cells. The first source is the undigested umbilical cord tissue. Because enzymatic digestion rarely digests the tissue completely, the remaining undigested tissue can be utilized as a seeding source for the expansion of mesenchymal stem cells. A second source for the derivation of mesenchymal stem cells is the Wharton's Jelly stem cells derived from the digested tissue. Enzymatic digestion cleaves collagen cross-links within the Wharton's Jelly and releases the embedded cells. As described previously, the released cells in the form of single-cell suspensions can be processed and cryopreserved for later therapeutic use. Alternatively, these cells can be used as a seeding source for the expansion of mesenchymal stem cells. In addition, the post-digestion cell-depleted Wharton's Jelly can be used as a supplement for the derivation of mesenchymal stem cells from both digested and undigested tissues. Its use as a supplement is not necessary for culture derivation but may reduce the time required for derivation and expansion.

In addition to the two-dimensional adherence culture routinely used for the expansion of mesenchymal stem cells, bioreactors may be used to expand mesenchymal stem cells in three-dimensional suspension cultures. Bioreactors allow for scaled-up production and closely mimic the in vivo perfusion characteristics of the umbilical cord. Mesenchymal stem cells can be derived initially from either two-dimensional or three-dimensional cultures and subsequently propagated in three-dimensional cultures for scaled-up production. The bioreactors may be supplemented with microcarrier beads to enable the adherence and propagation of the mesenchymal stem cells within the bioreactors.

EXAMPLES

The invention is further illustrated by the following examples, which are provided for illustrative purposes only, and should not be construed as limiting the scope or content of the invention in any way.

Example 1. Purification of Native Wharton's Jelly Stem Cells and Homogeneous Wharton's Jelly Solution Umbilical cords were collected in sterile specimen containers within 48 hours of the time of delivery. In a biosafety cabinet, 10 mL of Buffer B (50 µg/mL gentamicin, 100 units/mL penicillin and 100 µg/mL streptomycin in sterile Dulbecco's phosphate buffered saline) were added to the umbilical cord in an umbilical cord collection chamber. Other antibiotics, such as 0.25 µg/mL amphotericin B, 100 µg/mL streptomycin and/or 10 µg/mL ciprofloxacin, can also be added to Buffer B or substituted for any of the antibiotics in Buffer B. The contents of the collection chamber were then mixed by swirling and maintained at room temperature for fewer than 72 hours. The contents were swirled again for approximately 10-15 seconds to clean the umbilical cord tissue. Coagulated blood, if evident on the surface of the umbilical cord, was carefully removed using dissection tools.

The umbilical cord was transferred to a Petri dish using sterile forceps and cut into 3-5 cm segments using a sterile umbilical cord scissor or scalpel. Each segment was then individually dissected as follows. Briefly, a segment to be dissected was placed on a 150 mm Petri dish. The two arteries and one vein of the umbilical cord were located by viewing the cross-section of the tissue segment. Using dissecting scissors, an incision was made between the two arteries. With two tissue or Dumont forceps, the cord was pulled apart along the length of the tissue, carefully tearing the tissue away from the arteries and the vein. Once the tissue was opened, the vein was located and excised using a sterile fine point forceps in each hand. The two arteries were subsequently located and excised, and the dissected tissue was placed on the sterile, inside lid of the 150 mm dissection plate.

The tissue was then minced into small pieces/strands with dissecting scissors for at least 5 minutes or until a consistent minced tissue was obtained. The initial dissection and mincing were performed on different portions of the dissection plate to minimize contamination with excessive blood and/or dissected vessels. The final minced tissue looked like ground tissue and had no or few obvious tissue chunks. Generally, the minced tissue pieces had a cross-section of about 1 $mm^2$. The minced tissue was placed in a sterile, labeled conical tube.

Once all of the umbilical cord tissue segments were dissected, minced and added to the conical tube, 10 mL of solution CB (2.5 mg/mL collagenase NB6 (Serva) and 2 mM calcium chloride in Dulbecco's phosphate buffered saline) were also added. The contents of the tube were mixed by inverting/shaking several times until a uniform mixture was obtained. Parafilm was placed around the tube cap to prevent leakage and cross-contamination. The outside of the tube was sprayed with 70% ethanol and placed on an orbital shaker/mixer at approximately 175 RPM inside a 37° C. incubator for approximately two hours. Every hour the tube was shaken vigorously to help further dissociate the tissue. After approximately two hours, the tube was again sprayed with 70% ethanol and returned to the biosafety cabinet.

The digested tissue was then filtered using a Steriflip® filter unit (Millipore) to remove any undigested tissue from the digested tissue. As the digested Wharton's Jelly has a viscous, 'honey-like' consistency, care was taken to prevent contamination when opening caps and handling the jelly. The tube was placed upright, and its cap was removed carefully. To remove the jelly connecting the tube and the cap as completely and sterilely as possible, the tube and cap were pulled apart until small strands of the jelly followed. Circular motions then removed the final jelly strands from the cap. Care was taken not to contaminate the neck of the tube with the jelly. Once the cap was removed, 20 mL of Dulbecco's phosphate buffered saline were added to dilute the jelly. The cap was replaced and tightened, and the tube was inverted or shaken several times to mix. The cap was again removed carefully and the Steriflip® filter unit was screwed on the top of the tube and tightly secured. The assembly was then flipped over so that the 50 mL conical tube was upside down.

A regulated vacuum source was attached to the vacuum port on the side of the filter unit. The filter unit was maintained in an upright position while filtering. If needed, the tube/filter assembly was swirled vertically to dislodge tissue trapped in the filter. Once all liquid was filtered, the vacuum was shut off and the 50 mL conical tube was removed. 10 mL of Dulbecco's phosphate buffered saline were added to the 50 mL conical tube to wash any remaining cells that may have adhered to the sides or bottom of the tube. The cap of the tube was replaced and tightened and the tube was inverted or shaken several times to wash the bottom and sides of the tube. The cap was again removed and the tube again attached to the filter unit. The vacuum was reapplied until all liquid had passed through the filter, at which point the assembly was disconnected from the vacuum.

The total volume of the filtrate was approximately 50 mL. If needed, Dulbecco's phosphate buffered saline was added to the filtrate to bring the final volume to 50 mL. The cap was placed on the filtrate tube and tightly secured. The outside of the tube was sprayed with 70% alcohol and sealed with film to prevent leakage and cross-contamination. The tube was inverted/shaken several times until the jelly and the Dulbecco's phosphate buffered saline were homogenized. The tube was then placed on a shaker (at 175 RPM) in a 37° C. incubator for five minutes to further homogenize the jelly, with additional inversion/shaking as needed until a uniform mixture was obtained. The tube was again sprayed with 70% ethanol and returned to the biosafety cabinet.

The homogenized, digested Wharton's Jelly was then split into a number of 50 mL conical tubes depending on the initial weight of the umbilical cord. If the initial weight was no more than 15 grams, a single conical tube was used. If the initial weight was no more than 30 grams, two tubes were used. The number of tubes used was equal to the initial weight of the umbilical cord in grams, divided by 15, rounded up. Each tube received an approximately equal volume of the jelly; care was taken not to contaminate the necks of the tubes.

The volume of each tube was then brought to 50 mL with Dulbecco's phosphate buffered saline, and the contents of each tube were again homogenized. Subsequently, each tube was tightly capped; sprayed with 70% ethanol; sealed with film; inverted/shaken a number of times; and placed on a shaker (at 175 RPM) in a 37° C. incubator for five minutes to further homogenize the jelly, with additional inversion/shaking as needed until a uniform mixture was obtained.

Once homogenized, the tubes were spun for 20 minutes at 750×g at 37° C. After spinning a cell pellet was normally present at the bottom of each 50 mL tube. In the absence of a pellet, the tubes were respun at 1000×g for 15 minutes at 37° C. The tubes were sprayed with 70% ethanol and returned to the biosafety cabinet. The supernatant was decanted slowly, at a constant rate, without shaking or rocking the tube to avoid dislodging the pellet. The decanted supernatant, a homogenous Wharton's Jelly solution depleted of cells, was stored at or below −20° C. as a separate reagent useful for culturing stem cells.

To each cell pellet, 10 mL of Dulbecco's phosphate buffered saline were added. The tubes were securely capped and were vortexed, inverted, and/or pipetted several times to mix well until the cells were completely suspended. The contents of all sample tubes were then combined using a pipette into one tube. The sample tubes were rewashed with Dulbecco's phosphate buffered saline to dislodge any remaining cells, which were also added to the combined tube, and the volume was brought to 50 mL using Dulbecco's phosphate buffered saline. The tube was capped and vortexed/inverted several times to mix. The tube was spun for 15 minutes at 500×g at 37° C. A cell pellet was normally present at the bottom of the tube. In the absence of a pellet, the tube was respun at 750×g for 10 minutes at 37° C. The supernatant was carefully decanted into a waste flask so as not to disturb the cell pellet.

Subsequently, 25 mL of Dulbecco's phosphate buffered saline were added to the cell pellet and, after the tube was capped and vortexed/inverted several times to resuspend the cells, the cells were passed through a 70 micron tube-top filter. The filter was placed on top of a sterile 50 mL conical tube. The resuspended cells were released drop-wise from a sterile 25 mL pipette, directly above the center of the filter but not touching the filter. The filtered cell suspension collected in the 50 mL conical tube. An additional 20 mL of Dulbecco's phosphate buffered saline were used to wash the previous tube to maximize cell recovery; after washing the tube, these 20 mL were also passed dropwise through the filter. Additional Dulbecco's phosphate buffered saline was passed dropwise through the filter to bring the final volume to 50 mL.

The filtrate was spun for 10 minutes at 500×g at 37° C. A cell pellet was normally present at the bottom of the tube after the spin. In the absence of a pellet, the tube was respun at 750×g for 10 minutes at 37° C. The outside of the tube was sprayed with 70% alcohol before returning to the biosafety cabinet, where the supernatant was decanted off into a waste flask carefully, so as not to disturb the cell pellet. The volume in the tube was brought up to 4.3 mL using Dulbecco's phosphate buffered saline and the contents of the tube were mixed by pipetting, shaking, and/or vortexing. With a 1000 μL pipette, the cell suspension was mixed and a 0.3 mL aliquot was removed for quality control analysis, leaving 4.0 mL of a purified cell suspension of noncultured Wharton's Jelly stem cells.

Example 2. Storage of Noncultured Wharton's Jelly Stem Cells

The purified cell suspension of Example 1 was cryopreserved in a 25 mL freezing bag. Using a 60 mL syringe with an 18G needle, 16 mL of autologous plasma, 5% human serum albumin, or a combination thereof were added to the 4 mL purified Wharton's Jelly stem cell suspension. An alcohol pad was used to wipe the top of a vial of 55% DMSO/5% Dextran. Next, 5 mL of the DMSO/Dextran mixture were removed using a 60 mL syringe with an 18G needle and slowly added to the cell suspension. The cell suspension tube was capped tightly and gently inverted to mix, taking care not to make foam or bubbles. Using the same 60 mL syringe, 25 mL of the cell suspension were transferred to the freezing bag. The freezing bag was stored in a metal canister in a Styrofoam holder at −80° C. for 16 to 24 hours, optionally followed by an intervening period in a liquid nitrogen freezer in which the cells were exposed only to the vapor phase of the liquid nitrogen and, ultimately, in the liquid phase of liquid nitrogen for permanent storage. Alternatively, the freezing bag with cells can be permanently stored in the vapor phase of the liquid nitrogen.

Example 3. In Vivo Efficacy

The therapeutic efficacy of noncultured Wharton's Jelly stem cells was demonstrated in a co-transplantation assay with hematopoietic stem cells from umbilical cord blood to renew a mammalian hematopoietic system.

Hematopoietic stem cells from umbilical cord blood can be administered to a mammal to reconstitute a hematopoietic system damaged, for example, by radiation. Co-transplantation of Wharton's Jelly stem cells improves the reconstitution process, enhancing the engraftment of the administered hematopoietic stem cells and, therefore, their ability to proliferate and recreate a hematopoietic system in their new host.

To test the efficacy of noncultured Wharton's Jelly stem cells, they were co-administered with hematopoietic stem cells from umbilical cord blood to (NOD/SCID IL2Rγ-null) mice that had been sublethally irradiated the day before with 300 cGy of gamma-radiation which ablated the bone marrow. 1,000,000 mononuclear umbilical cord blood cells were administered to the mice via the tail vein, either alone or with 10,000, 50,000, or 100,000 noncultured Wharton's Jelly stem cells, or with 1,000,000 mesenchymal stem cells cultured from Wharton's Jelly. Sixty days later, the bone marrow was obtained from the mice to measure the number of cells expressing human CD45, a cell surface marker for human hematopoietic cells and a surrogate marker for human hematopoietic stem cell engraftment.

As shown in FIG. 1, irradiated mice which did not receive any cells lacked human CD45-expressing cells in their bone marrow on day 60. Although mice receiving only mononuclear umbilical cord blood cells showed a substantial number of bone marrow cells expressing human CD45, this number more than tripled in mice that received mesenchymal stem cells cultured from Wharton's Jelly or noncultured Wharton's Jelly stem cells. Surprisingly, 100,000 noncultured Wharton's Jelly stem cells provided a benefit equal to or greater than the benefit of 1,000,000 culture-expanded mesenchymal stem cells from Wharton's Jelly, suggesting that noncultured Wharton's Jelly stem cells may be more than ten-fold more potent in vivo than cultured mesenchymal stem cells. In fact, as few as 10,000 noncultured Wharton's Jelly stem cells were nearly as effective as 1,000,000 cultured mesenchymal stem cells. While the precise mechanism for the reduced efficacy of cultured mesenchymal stem cells is unclear, minimally manipulated, uncultured Wharton's Jelly stem cells appear to have important therapeutic advantages in vivo.

Example 4. Differences in Cell Surface Marker Profiles

Noncultured Wharton's Jelly stem cells are also noticeably different at the molecular level from mesenchymal stem cells cultured from Wharton's Jelly.

Figure 2:
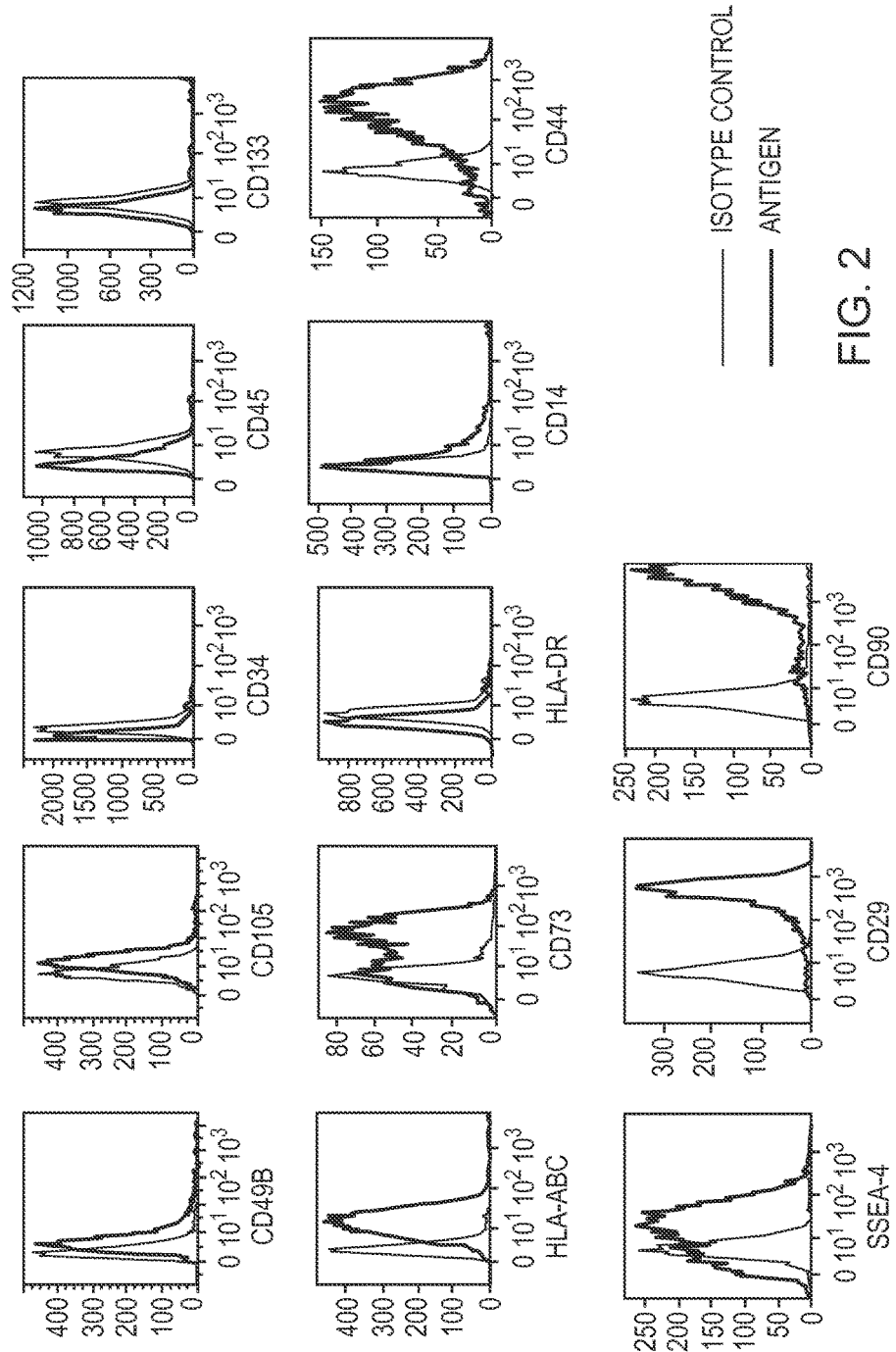
FIG. 2 graphically depicts, for each of thirteen cell surface markers (CD49B, CD105, CD34, CD45, CD133, HLA-ABC, CD73, HLA-DR, CD14, CD44, SSEA-4, CD29 and CD90), in two-dimensions the number of noncultured Wharton's Jelly stem cells measured to have a particular expression level of the marker on the cell surface.

The levels of thirteen cell surface markers on a population of noncultured Wharton's Jelly stem cells were assayed by standard antibody/flow cytometry assays, and the results are depicted in FIG. 2. FIG. 2 provides, for each marker tested, a standard two-dimensional representation showing the percentage of cells demonstrating a particular expression level of the marker, as detected by antibody assay. The results from the noncultured Wharton's Jelly stem cells are represented with a dark line, and the results from a control are represented with a lighter line. As shown, noncultured Wharton's Jelly stem cells exhibited higher levels of CD49B, CD105, HLA-ABC, CD73, CD44, SSEA-4, CD29, and CD90 compared to the antigen control. Noncultured Wharton's Jelly stem cells did not demonstrate substantial expression of CD34 and CD45, markers that would be typical of hematopoietic cells, or of CD14, HLA-DR or CD133.

Figure 3:
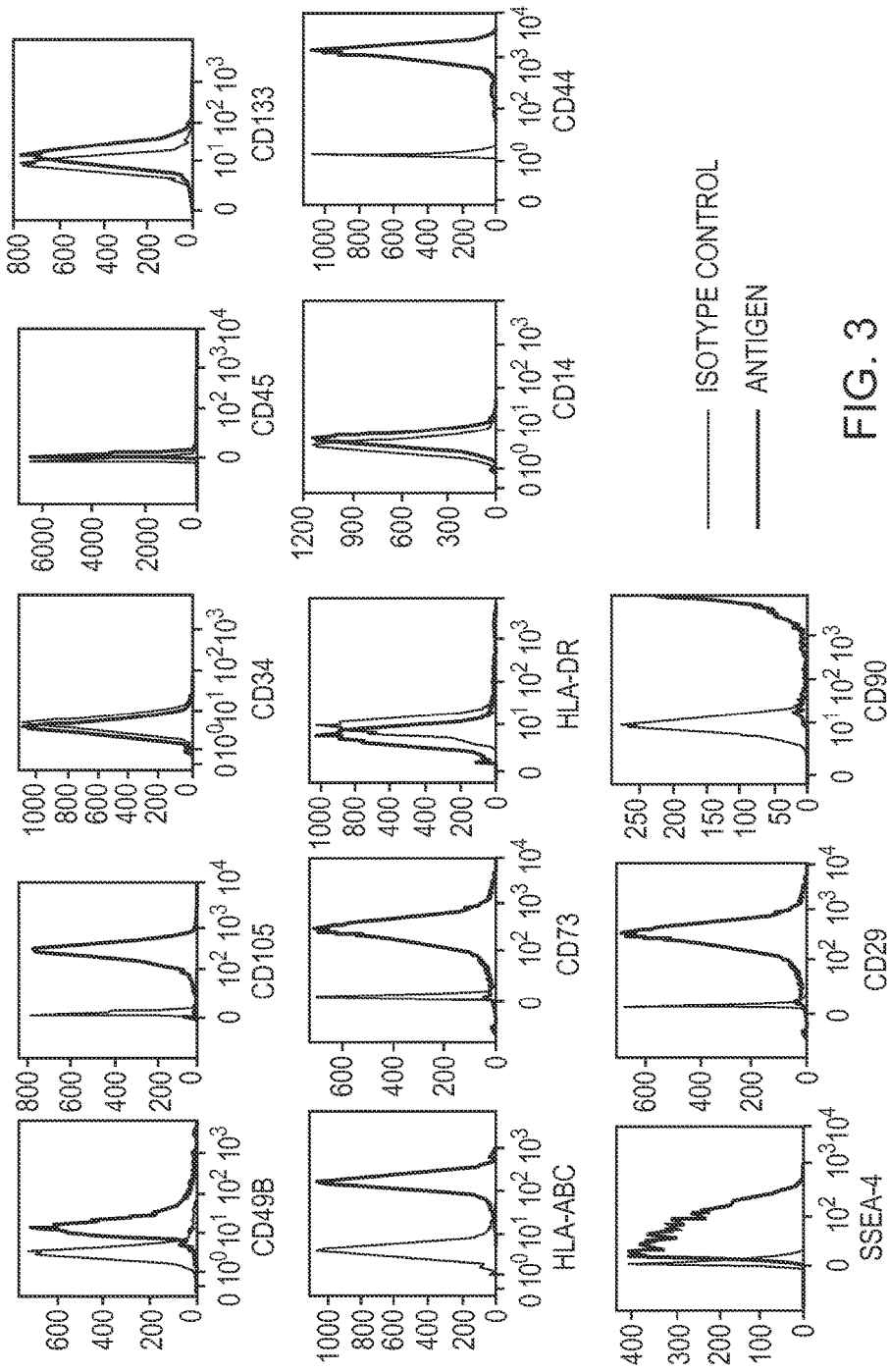
FIG. 3 is a comparable graphical depiction of the number of culture-expanded mesenchymal stem cells from Wharton's Jelly having a particular expression level of the marker on the cell surface.

The expression of the same markers was tested in mesenchymal stem cells cultured from Wharton's Jelly; the results are depicted in FIG. 3. As shown, compared to the antigen control, cultured mesenchymal stem cells demonstrated higher levels of CD49B, CD105, HLA-ABC, CD44, CD29, CD73 and CD90; a broader range of levels of expression of SSEA-4; and a lack of CD14, CD34, CD45, and HLA-DR. Comparing FIG. 2 and FIG. 3, even for markers such as CD105 which are elevated both in cultured mesenchymal stem cells and in noncultured Wharton's Jelly stem cells, the patterns of expression can be very different, as the observed levels of expression in noncultured Wharton's Jelly stem cells substantially overlap with the antigen control, whereas the mesenchymal stem cells cultured ex vivo show much higher levels of expression with little overlap with the antigen control. Thus, cells that have been purified from Wharton's Jelly without culturing are not merely particularly potent in vivo, they are also markedly different from mesenchymal stem cells cultured and expanded from Wharton's Jelly as evidenced by their patterns of cell surface markers.

INCORPORATION BY REFERENCE

The entire disclosures of each of the patent documents and scientific articles cited herein are incorporated by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

I claim:

1. A method of culturing mesenchymal stem cells, the method comprising:
    (a) mincing umbilical cord tissue comprising Wharton's Jelly;
    (b) subsequently diluting the umbilical cord tissue;
    (c) subsequently filtering the umbilical cord tissue to generate a filtrate;
    (d) sedimenting Wharton's Jelly stem cells from the filtrate to generate a cell-depleted Wharton's Jelly filtrate; and
    (e) culturing mesenchymal stem cells in a medium comprising the cell-depleted Wharton's Jelly filtrate.

* * * * *